United States Patent [19]

Kihlberg et al.

[11] Patent Number: 5,213,096
[45] Date of Patent: May 25, 1993

[54] APPARATUS FOR CONNECTING A PATIENT TO BREATHING DEVICES, THE APPARATUS INCLUDING A BACTERIA FILTER AND GAS SAMPLING MEANS

[75] Inventors: Ake Kihlberg, Täby; Ragnar Tryggvason, Löddeköpinge; Per Wikefeldt, Järfälla, all of Sweden

[73] Assignee: Gambro Engstrom AB, Sweden

[21] Appl. No.: 942,368

[22] Filed: Sep. 9, 1992

Related U.S. Application Data

[63] Continuation of Ser. No. 698,717, May 10, 1991, abandoned.

[30] Foreign Application Priority Data

Jun. 18, 1990 [SE] Sweden ............................. 90021627
Nov. 2, 1990 [SE] Sweden ............................. 90035056

[51] Int. Cl.$^5$ .................. A62B 7/10; A62B 19/00; A62B 23/02; A61B 5/08
[52] U.S. Cl. ................. 128/205.12; 128/730; 128/DIG. 26; 128/912; 128/205.29
[58] Field of Search ............. 128/207.15, 207.17, 128/205.12, 201.13, DIG. 26, 912, 911, 204.18, 205.27, 205.28, 205.23, 200.24, 730, 202.27, 205.29

[56] References Cited

U.S. PATENT DOCUMENTS

| 3,713,440 | 1/1973 | Nicholes | 128/205.12 |
|---|---|---|---|
| 3,935,110 | 1/1976 | Schmid et al. | 210/445 |
| 4,020,849 | 5/1977 | Jackson | 128/207.15 |
| 4,090,513 | 5/1978 | Togawa | 128/205.23 |
| 4,200,094 | 4/1980 | Gedeon et al. | 128/201.13 |
| 4,360,018 | 11/1982 | Choksi | 128/205.12 |
| 4,485,822 | 12/1984 | O'Connor et al. | 128/207.17 |
| 4,516,573 | 5/1985 | Gedeon | 128/204.18 |
| 4,557,261 | 12/1985 | Rugheimer | 128/912 |
| 4,774,940 | 10/1988 | Linder | 128/204.18 |
| 4,829,998 | 5/1989 | Jackson | 128/204.18 |
| 4,838,258 | 6/1989 | Dryden et al. | 128/204.18 |
| 4,852,563 | 8/1989 | Gross | 128/204.18 |
| 4,924,860 | 5/1990 | Larsen et al. | 128/205.12 |

FOREIGN PATENT DOCUMENTS

| 0265163 | 4/1988 | European Pat. Off. | 128/205.12 |
|---|---|---|---|
| 352415 | 5/1989 | European Pat. Off. | |
| 3339988 | 5/1985 | Fed. Rep. of Germany | 128/912 |
| 3702917 | 8/1988 | Fed. Rep. of Germany | 128/912 |
| 2386314 | 12/1978 | France | 128/201.13 |
| 399359 | 2/1978 | Sweden | |
| 449441 | 5/1987 | Sweden | |
| 8154 | of 1907 | United Kingdom | |
| 2233904 | 1/1991 | United Kingdom | 128/201.13 |

Primary Examiner—Edgar S. Burr
Assistant Examiner—Kimberly L. Asher
Attorney, Agent, or Firm—Lerner, David, Littenberg, Krumholz & Mentlik

[57] ABSTRACT

Apparatus for connecting a patient to a breathing device such as a respirator, anesthesia machine or the like is disclosed, including a Y-piece including a patient attachment tube, and a pair of additional attachment tubes adapted for connection to an inhalation tube and an exhalation tube, respectively, and including a bacteria filter disposed within the apparatus and separating the patient attachment tube from the two additional attachment tubes so that gases passing between the patient attachment tube and these two attachment tubes along a predetermined flow path must pass through the bacteria filter. In one embodiment the apparatus includes a partition wall arranged for separating inhaled air and exhaled air during passage through the Y-piece.

81 Claims, 6 Drawing Sheets

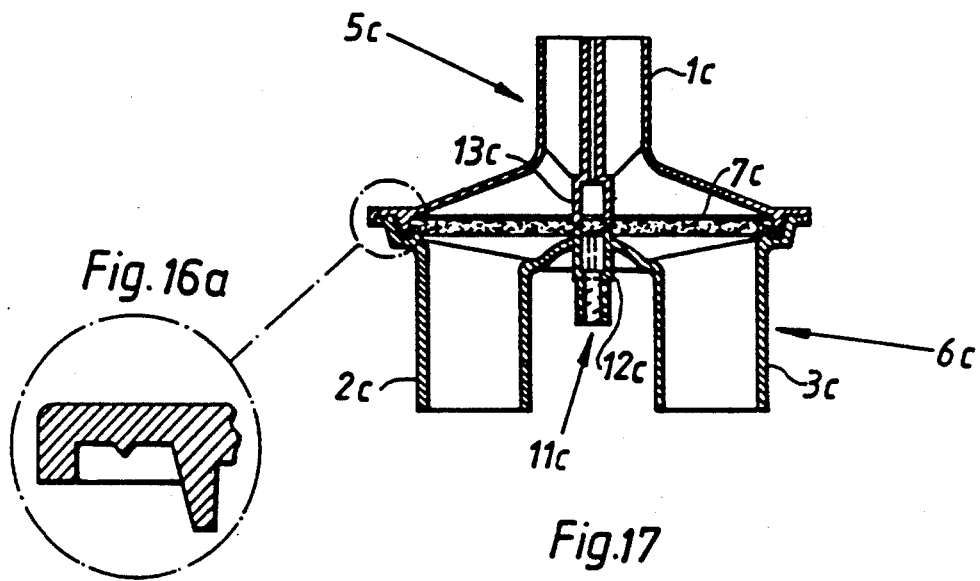
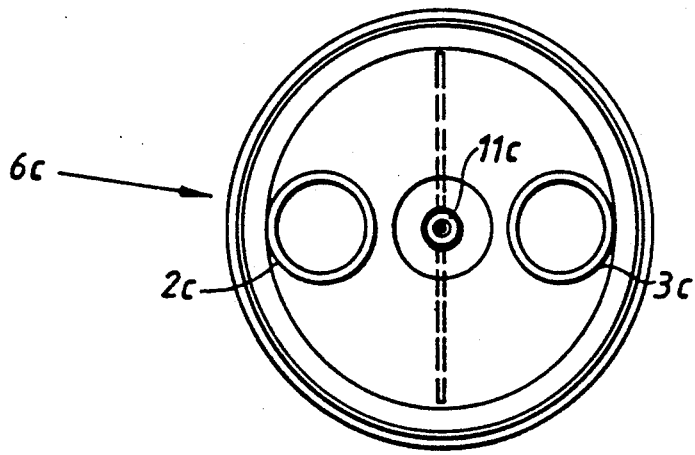
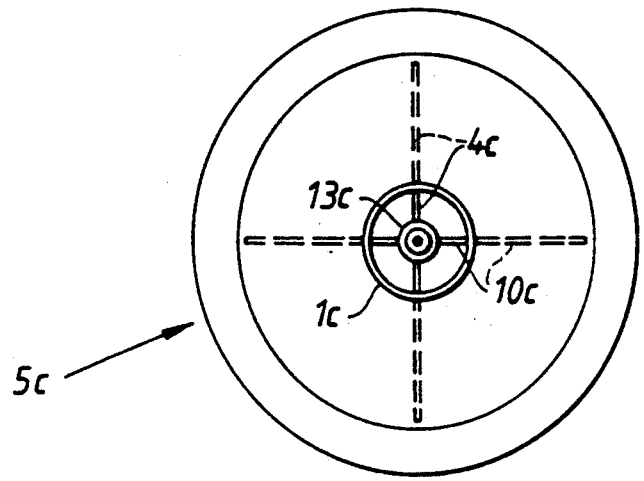

APPARATUS FOR CONNECTING A PATIENT TO BREATHING DEVICES, THE APPARATUS INCLUDING A BACTERIA FILTER AND GAS SAMPLING MEANS

This is a continuation of application Ser. No. 07/698,717 filed May 10, 1991, now abandoned.

FIELD OF THE INVENTION

The present invention relates to apparatus for connecting patients to breathing devices. More particularly, the present invention relates to apparatus for connecting patients to respirators, anesthesia machines and the like.

Still more particularly, the present invention relates to such apparatus including a Y-piece which includes an attachment nipple directed to the patient and two attachment nipples for attachment to an inhalation tube and an exhalation tube, respectively.

BACKGROUND OF THE INVENTION

As used in connection with the present application, the expression "Y-piece" also includes shapes other than that of conventional "Y." Of significance is only the fact that the patient attachment piece can be connected to an inhalation and exhalation tube, respectively. The expression "Y-piece" thus also includes, for example, T-connectors and connectors for coaxially connecting arranged inhalation and exhalation tubes.

In addition, the term "patient attachment piece" is also used in connection with this application. The "patient attachment piece" is intended to be attached to the portion of the Y-piece which is directed towards the patient. These patient attachment pieces can, for example, be designed in accordance with U.S. Pat. No. 4,516,573. In this patent there is thus described a bellowed patient attachment piece, which contains a wad of moisture- and heat-absorbing material. In this manner, heat and moisture are taken up from the exhaled gas and provided to the inhaled gas. Such patient attachment pieces are often connected with various types of Y-pieces and may be equipped with various types of bacterial filters. The more components which are connected, however, lead to a bulkier construction, which can thus become rather inconvenient for the patient. Furthermore, the connection of a number of different components creates the risk of both leakage and, on the other hand, improperly connected components.

When a patient is attached to a respirator, anesthesia machine or the like, there also arises a need for continuous or intermittent sampling of the exhaled gas and for proximal pressure measuring. This should take place as close to the patient as possible, and can occur, for example, in the manner described in U.S. Pat. No. 4,838,258; i.e., by means of a tube which extends from the respirator itself, through the exhalation tube, to a point near the patient. The disadvantage with this construction, however, is that the withdrawn sample can be, on the one hand, extremely moist, and. on the other hand, contaminated with bacteria.

Furthermore, in the case of conventional Y-pieces, a certain dead volume must be taken into account. By dead volume is meant the quantity of exhaled gases which return to the patient. This dead volume rapidly increases if the Y-piece is provided with extra functions, such as with a bacteria filter, as described, for example, in Swedish Patent Application No. 90.02162/7, filed Jun. 18, 1990.

SUMMARY OF THE INVENTION

In accordance with the present invention, apparatus has now been discovered for connecting a patient to breathing devices, such as respirators and anesthesia machines, comprising a patient attachment tube member extending in a first direction and having a first end and a second end, first and second attachment tube members extending in a second direction, said first and second attachment tube members being adapted for connection to an inhalation tube and an exhalation tube, respectively, and each including a first end and a second end, said second direction being different from said first direction such that said first end of said patient attachment tube member is proximate to said first ends of said first and second attachment tube members and said second end of said patient attachment tube member is distal from said second ends of said first and second attachment tube members, connecting means connecting said first end of said patient attachment tube member to said first ends of said first and second attachment tube members, and a bacteria filter disposed within said apparatus and separating said first end of said patient attachment tube member from said first ends of said first and second attachment tube members, whereby gases passing between said patient attachment tube member and said first and second attachment tube members along a predetermined flow path must pass through said bacteria filter.

In accordance with one embodiment of the apparatus of the present invention, the apparatus includes a patient attachment element attached to the patent attachment tube member for use by the patient, and the apparatus has a flow-through area which is greater than the flow-through area of the patient attachment element.

In accordance with another embodiment of the apparatus of the present invention, the patient attachment tube member comprises a first part of the apparatus, and the first and second attachment tube members comprise a second part of the apparatus, the first and second parts being attached to each other to form the connecting means with the bacteria filter therebetween.

The present invention relies in considerable part in the bacteria filter being arranged within the apparatus or Y-piece itself. In order to reduce breathing resistance therein, the flow-through area of the Y-piece can thus be enlarged in comparison to that of the patient attachment piece. By reducing the number of parts included in the connection arrangement itself, choking can be reduced, since this can easily occur with the apparatus used in the past in which a number of components are connected together.

In accordance with one construction of the present invention, which is relatively simple, particularly in terms of the ability to manufacture same, the Y-piece is formed from two bowl-shaped parts, and the bacteria filter is clamped between these parts substantially perpendicular to the flow-through direction or the above-mentioned predetermined flow path.

In accordance with this aspect of the present invention, the Y-piece normally includes three attachment nipples; namely, one for patient attachment piece, one for the inhalation tube, and one for the exhalation tube. From the point of view of manufacturing, a particularly suitable construction is obtained when these nipples are arranged substantially parallel to each other. Thus, in accordance with this embodiment of the present invention, the patient attachment tube member and the first and second attachment tube members comprise such nipples extending substantially parallel to each other.

In accordance with another embodiment of the apparatus of the present invention, the apparatus has a substantially circular configuration, so as to maximize the flow-through area of the apparatus in proportion to its volume, while at the same time the length of the apparatus and the direction of the flow is restricted to that which its function permits.

In accordance with a preferred embodiment of the apparatus of the present invention, the apparatus includes sample withdrawal means for obtaining a gas sample from the apparatus during exhalation therethrough. This gas sample is thus provided in the flow direction for exhalation downstream of the bacteria filter. In this manner, considerably dryer gas samples can be obtained without secretions from the patient. The proximal pressure of the patient can also be measured through this outlet.

In a preferred embodiment the sample withdrawal means is located on the opposite side of the bacteria filter as compared to the patient attachment tube member.

In accordance with a preferred embodiment of the apparatus of the present invention, a patient attachment element is attached to the patient attachment tube member, preferably comprising a flexible tubular member which more preferably contains a heat and moisture exchange medium which is preferably in the form of a wad or the like of flexible material such as fibers, and which has the ability to take up heat and moisture from exhaled gas and subsequently deliver this heat and moisture to the inhaled gas. The manner in which this is achieved is described in more detail in U.S. Pat. No. 4,516,573, the disclosure of which is incorporated herein by reference thereto.

In accordance with a preferred embodiment of the apparatus of the present invention, the sample withdrawal means is preferably arranged in the form of a nipple which is substantially in the middle of the Y-piece which, in a direction perpendicular to the flow-through direction, has a somewhat drawn-out flow-through area, such as being substantially oval or having a rounded rectangular-shaped configuration, and is preferably located between the attachment nipples for the inhalation and exhalation tubes, and is preferably parallel thereto.

In an alternate embodiment, however, the sample withdrawal outlet can have the form of a nipple which is angled with respect to the other nipples. In both cases, however, it is important that the sample withdrawal outlet be shieldably arranged between the attachment nipples for the inhalation and exhalation tubes, respectively.

In accordance with a preferred embodiment of the apparatus of the present invention, the sample withdrawal means includes first tube means extending into contact with the bacteria filter. Preferably, the sample withdrawal means includes second tube means located on the same side of the bacteria filter as the patient attachment tube member, and the second tube means also extends into contact with the bacteria filter.

In a preferred embodiment, the second tube means extends into the patient attachment tube member, and preferably the first and second tube means are located on opposite sides of the bacteria filter, and are both in pressure contact therewith. Preferably, the first and second tube means each include widened portions at the ends of the first and second tube means which are in contact with the bacteria filter, and preferably these widened portions comprise cone-shaped or cylindrical configurations.

The Y-pieces of the present invention require a certain minimum volume. By way of example, the attachment nipples should have a certain standard dimension. In order for this volume to affect the withdrawal sample as little as possible, the sample withdrawal outlet is thus suitably connected to a first sample withdrawal tube which extends from the outlet to the bacteria filter, and which can, via the bacteria filter, be connected to a second sample withdrawal tube which extends from the filter towards the patient attachment piece, and which preferably extends up to and possibly into this patient attachment piece. In this manner, the effect of the inner volume of the Y-piece on the sample withdrawal tube is substantially eliminated.

As indicated above, the sample withdrawal means preferably is further simplified when the first and second withdrawal tubes are arranged on either side of the bacteria filter and are in pressured contact therewith by means of widened portions, such as cone-shaped and/or cylindrical funnel-like portions which are at right angles to the direction of flow. In this manner, the simplification of flow of the sample through the bacteria filter is achieved while leakage between the inner sample withdrawal tube and the atmosphere surrounding it is substantially prevented.

In accordance with another embodiment of the apparatus of the present invention, the first and second parts thereof include bowl-shaped inner surfaces in contact with the bacteria filter, and at least the second part, which comprises the first and second attachment tube members, includes web means for supporting the sample withdrawal means therein.

In accordance with another embodiment of the apparatus of the present invention, patient attachment element also serves as a heat and moisture exchanger by being equipped with a wad or the like of the above-mentioned type. In a preferred embodiment, the wad of flexible material is impregnated with an anti-bacterial agent, such as clorhexidine or hydrogen peroxide, and or with a hygroscopic substance, such as magnesium chloride, lithium chloride and calcium chloride.

In accordance with a preferred embodiment of the apparatus of the present invention, the wad of flexible material comprises fibers of plastic material having a first melting point, and they are coated with a plastic material having a second melting point, the second melting point being lower than the first melting point, whereby the fibers are bonded by heating the fibers to the second melting point.

Preferably, the fibers of plastic material having a first melting point comprise polypropylene and the plastic material having a second melting point comprises polyethylene. In this manner, the breaking off of material from the fiber wad and its transmittal into the patient's respiratory organs is effectively prevented.

In accordance with another embodiment of the apparatus of the present invention, the patient attachment element includes at least a portion comprising transparent material, which portion is free of any added material within the interior thereof, so as to serve as a secretion trap or inspection zone therefor. This portion of the patient attachment element is preferably located nearest the patient.

In certain embodiments, however, such as in connection with anesthesia treatments, the patient attachment piece is not required. This is therefore suitably arranged to be disconnectable from the Y-piece or patient attachment tube member thereof.

In accordance with another embodiment of the apparatus of the present invention, both the first and second parts include web means for supporting the sample withdrawal means.

In accordance with another embodiment of the apparatus of the present invention, the apparatus includes partition means extending from a point between the first and second attachment tube members towards the patient attachment tube member, so as to separate inhaled air and exhaled air during their respective passage through the apparatus in the predetermined flow direction.

Preferably, the partition means extends at least up to the bacteria filter. More preferably, in the embodiment where the patient attachment tube member comprises a first part of the apparatus and the first and second attachment tube members comprise a second part of the apparatus, both the first and second parts include partition means, whereby the partition means is located on either side of the bacteria filter so as to clamp and support the bacteria filter therebetween. Preferably, the partition means on both the first and second parts includes a first partition means portion and a second partition means portion. In this manner, both of the preferably bowl-shaped portions of the Y-piece are provided with internal stiffening webs which are arranged so as not to disturb the flow-through as much as possible, such as by being radially directed in relation to the principal flow-through direction, while also being arranged to support the bacteria filter on both sides thereof.

In accordance with another embodiment of the apparatus of the present invention, the patient attachment tube member includes a collar member concentrically located therewithin for facilitating connection to various attachment parts, either exteriorly or interiorly of the patient attachment tube member, the partition means extending only between the collar member and the patient attachment tube member.

In accordance with the present invention, apparatus is also provided for connecting a patient to breathing devices comprising a patient attachment element, a Y-piece for connecting the patient attachment element to an inhalation tube and an exhalation tube, the Y-piece including a bacteria filter therein, and a sample withdrawal member located downstream of the bacteria filter with respect to the patient attachment element, the sample withdrawal member including a sample withdrawal tube extending towards the bacteria filter for contact therewith, so that bacteria-free samples can be obtained from the sample withdrawal means through the bacteria filter.

In order that samples can thus be taken from a location as close to the patient as possible, the first sample withdrawal tube can be connected, through the bacteria filter, to a second sample withdrawal tube which extends from the bacteria filter towards the patient attachment piece, and preferably up to and possibly into the patient attachment piece. The filtering of the withdrawn samples is thereby simplified if the first and second sample withdrawal tubes are arranged on either side of the bacteria filter and are in pressurized contact therewith by means of widened portions, such as the cone-shaped and/or cylindrical funnel-like portions, and preferably at right angles to the flow direction discussed hereinabove.

The moisture content of the withdrawn samples therefrom is reduced if the patient attachment piece thus contains a heat and moisture exchange system in the form of a wad or the like of a flexible material such as fibers, which has the ability to withdraw heat and moisture from exhaled gases and subsequently deliver same to the inhaled gases. Preferably, the complete patient attachment piece is made from a flexible material.

BRIEF DESCRIPTION OF THE DRAWINGS

The following detailed description of the present invention can be more readily appreciated with reference to the drawings, in which:

FIG. 16 is a side, elevational, sectional view of another apparatus in accordance with the present invention;

FIG. 16a is a partial, side, sectional, enlarged view of a portion of the apparatus shown in FIG. 16;

FIG. 17 is a bottom, elevational view of the apparatus shown in FIG. 16; and

FIG. 18 is a top, elevational view of the apparatus shown in FIG. 16.

DETAILED DESCRIPTION

Figure 1:
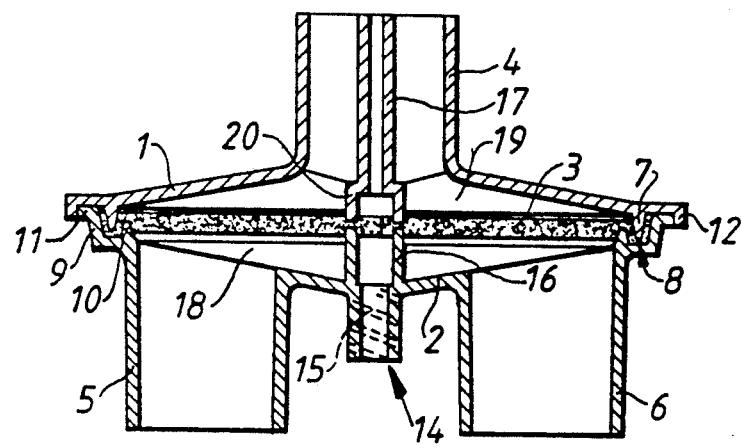
FIG. 1 is a side, elevational, sectional view of a Y-piece comprising an embodiment of the apparatus of the present invention.
Figure 2:
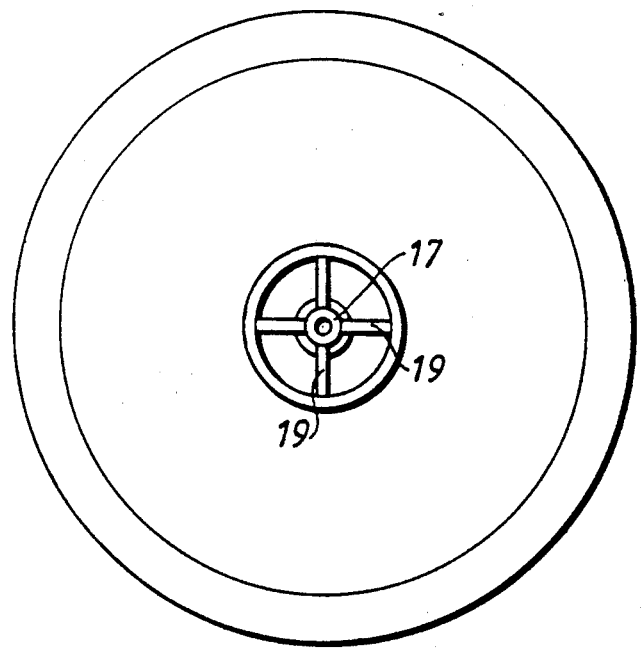
FIG. 2 is a top, elevational view of the apparatus shown in FIG. 1.

Turning to the Figures, in which like numerals refer to like portions thereof, FIGS. 1 and 2 show sectional and end views, respectively, of a Y-piece which is intended to be included in the connection arrangement according to the present invention.

The Y-piece shown in FIGS. 1 and 2 comprises two bowl-shaped parts, 1 and 2, with a bacteria filter 3 clamped therebetween. The upper bowl-shaped part 1 is provided with a nipple 4 which is intended to be connected to a patient attachment piece. The lower bowl-shaped part 2 is provided with two parallel nipples, 5 and 6, which are intended to be connected to an inhalation tube and an exhalation tube, respectively, which are, in turn, intended to be connected to a respirator, anesthesia machine or the like.

The bacteria filter 3 is clamped between a circular ridge 7 on the upper bowl-shaped part 1, and a circular groove 8 in the lower bowl-shaped part 2. This groove 8 is formed from an outer flange 9 and an inner ridge 10. The flange 9 is terminated at its outer portion by a radially extending partial flange 11, which is intended to be fixed to the upper bowl-shaped part 1 by, for example, glueing or welding, and preferably by ultrasonic welding. The concentricity of the two bowl-shaped parts, 1 and 2, is facilitated by an outer peripheral flange 12 on the upper bowl-shaped part 1.

The lower bowl-shaped part 2 further comprises a sample withdrawal outlet in the form of a nipple 14, which is preferably provided with an inner or outer screw thread 15, or other such fixing means. The nipple 14 is connected to a first sample withdrawal tube 16 which, in turn, via filter 3, is connected to a second sample withdrawal tube 17. Both of these sample withdrawal tubes, as well as the filter 3, are supported by radially extending support webs 18 and 19, respectively. The sample withdrawal tube 17 terminates on its inner end with a widened cylindrical portion 20, which, via the filter 3, presses against a corresponding portion of the sample withdrawal tube 16. As is evident from FIG. 2, the sample withdrawal tube 17 is located between four radially directed support webs 19.

Figure 3:
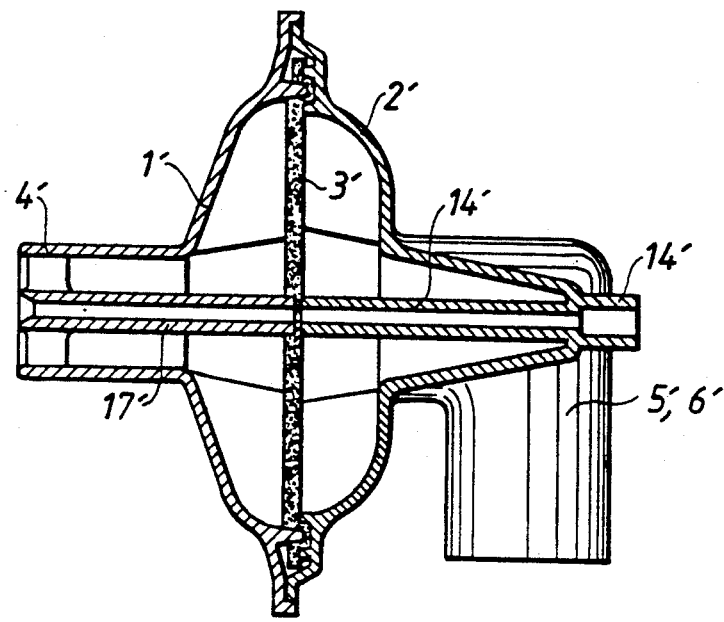
FIG. 3 is a side, elevational, partially sectional view of another embodiment of the apparatus of the present invention.
Figure 4:
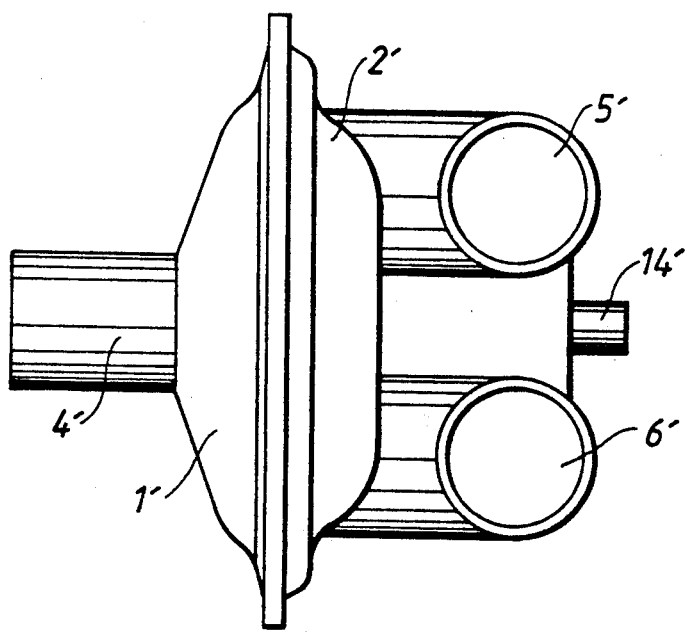
FIG. 4 is a bottom, elevational view of the apparatus shown in FIG. 3.
Figure 6:
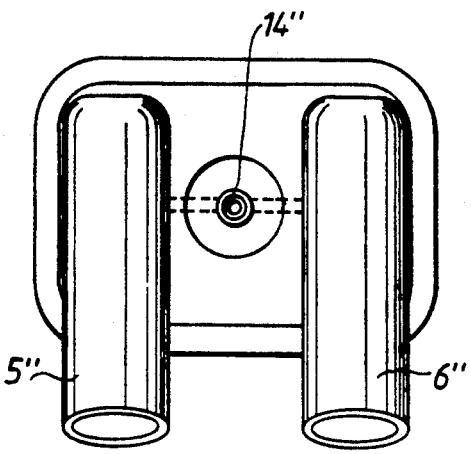
FIG. 6 is a front, partially plan view of the apparatus shown in FIG. 5.
Figure 5:
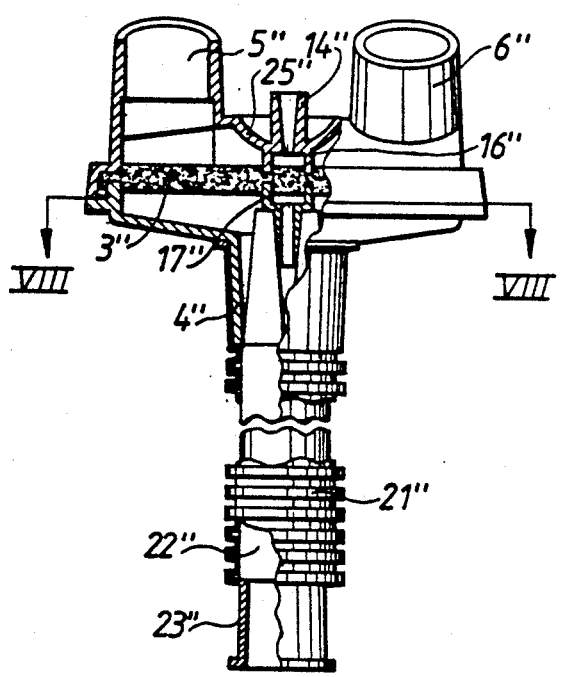
FIG. 5 is a bottom, elevational, partially sectional view of another apparatus in accordance with the present invention.
Figure 7:
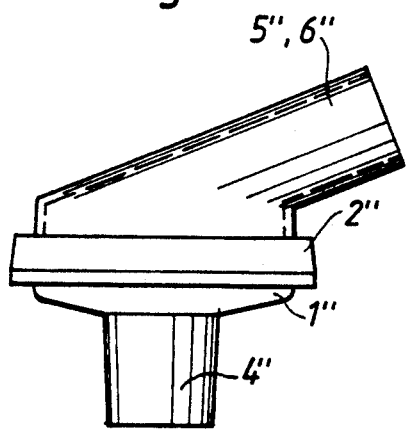
FIG. 7 is a side, elevational, partially plan view of the apparatus shown in FIG. 5.
Figure 8:
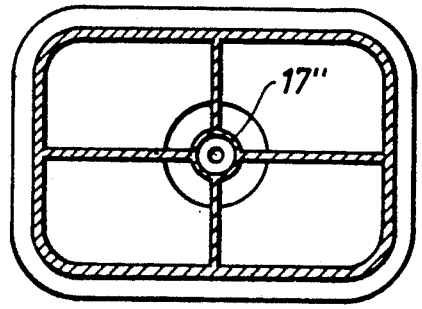
FIG. 8 is an elevational, cross-sectional view of the apparatus shown in FIG. 5 taken along line VIII—VIII thereof, with the filter removed.
Figure 10:
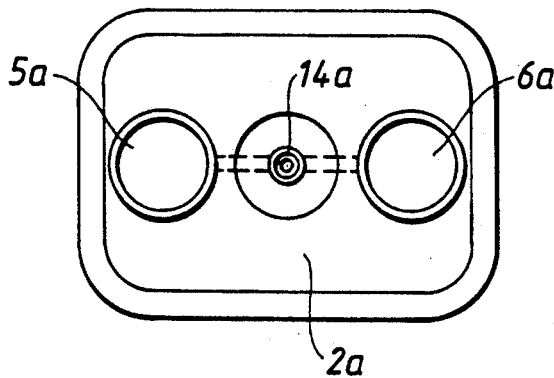
FIG. 10 is a front, elevational, partially plan view of the apparatus shown in FIG. 9.
Figure 9:
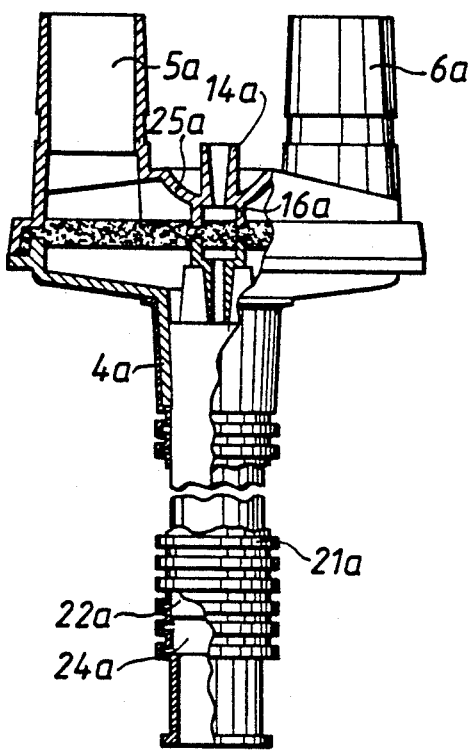
FIG. 9 is a bottom, elevational, partially sectional view of another apparatus in accordance with the present invention.
Figure 11:
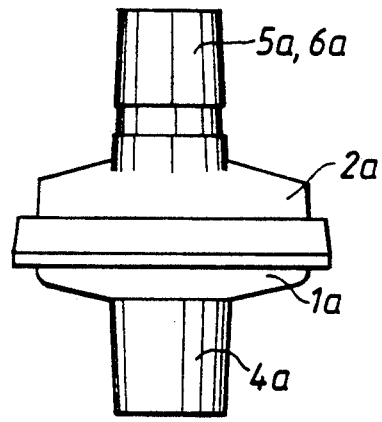
FIG. 11 is a side, elevational, partially plan view of the apparatus shown in FIG. 9.
Figure 12:
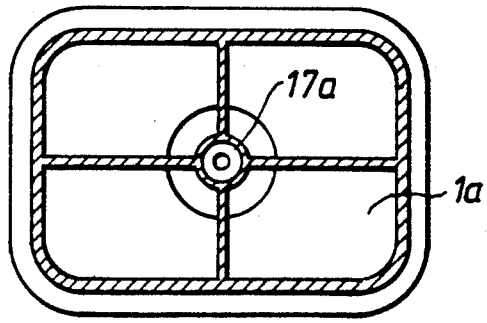
FIG. 12 is an elevational, cross-sectional view of the apparatus shown in FIG. 9 with the filter removed therefrom.

Turning to FIGS. 3 and 4, there is shown a modified embodiment of a Y-piece in the connection arrangement according to the present invention. This construction corresponds in principle with that according to FIGS. 1 and 2. Thus, the same reference numerals have been used, but with the addition of a prime mark. The most significant difference is that the attachment nipples 5' and 6', respectively, are angularly formed. Furthermore, the sample withdrawal tubes 16' and 17' in this case have been given a somewhat different shape.

In FIGS. 5 through 8, there is shown a somewhat more complete construction of an embodiment of the connection arrangement according to the present invention. Once again, this embodiment generally corresponds with the embodiment discussed above. Thus, the same reference numerals are employed with respect to corresponding details therein, but with the addition of a double prime mark. Reference numerals 5" and 6" thus denote two nipples which are intended to be attached to an inhalation tube and an exhalation tube, respectively. The bacteria filter itself is denoted by reference numeral 3". Reference numeral 14" denotes a sample withdrawal nipple which is connected to a first sample withdrawal tube 16". This sample withdrawal tube 16" is, in turn, via filter 3", in contact with a second sample withdrawal tube 17". Reference numeral 4" denotes a nipple by means of which the Y-piece is connected to a patient attachment piece 21". This patient attachment piece 21" is preferably designed substantially in accordance with the description in U.S. Pat. No. 4,516,573. It is, however, preferably of uniform thickness. Within the patient attachment piece there is preferably a wad 22" or the like of a moisture- and heat-absorbing material which serves to take up heat and moisture from the exhaled gas and pass same to the inhaled gas. Finally, in FIG. 5, reference numeral 23" denotes an attachment pipe or cone by means of which the patient attachment piece 21" can be connected to a tracheal tube or the like.

The Y-piece shown in FIGS. 5 through 8 also consists of two bowl-shaped parts 1" and 2", respectively, but differs from the above-described Y-pieces in that, for example, these parts have been given a rectangular shape with rounded edges or corners. Furthermore, the attachment nipples 5' and 6' are arranged at a different angle as compared, for example, to that shown in FIGS. 3 and 4. Finally, reference numeral 25' denotes a dome which is directed towards the interior of the Y-piece and within which the sample withdrawal nipple 14' is arranged. In light of this arrangement, the Y-piece's inner volume is reduced, while the sample withdrawal tube 16' is stabilized.

The construction according to FIGS. 9 through 12 substantially corresponds to that according to FIGS. 5 through 8, and corresponding details thereof have thus been given the same reference numerals, but with the suffix a instead of the double prime marks used in FIGS. 5 through 8. The construction according to FIGS. 9 through 12 differs from that according to FIGS. 5 through 8 in that the nipples 5a and 6a are arranged parallel to the nipple 4a. Furthermore, the fiber wad 22a does not fill the entire patient attachment piece 21a. In this case, a free space 24a is left nearest to the patient, and is intended to serve as a secretion trap, and can also serve as an inspection zone if the patient attachment piece is made from a transparent material. Finally, reference numeral 25a denotes a dome which is directed towards the interior of the Y-piece, and within which the sample withdrawal nipple 14a is arranged. In light of this arrangement, the Y-piece's inner volume is reduced, while the sample withdrawal tube 16a is stabilized.

Figure 13:
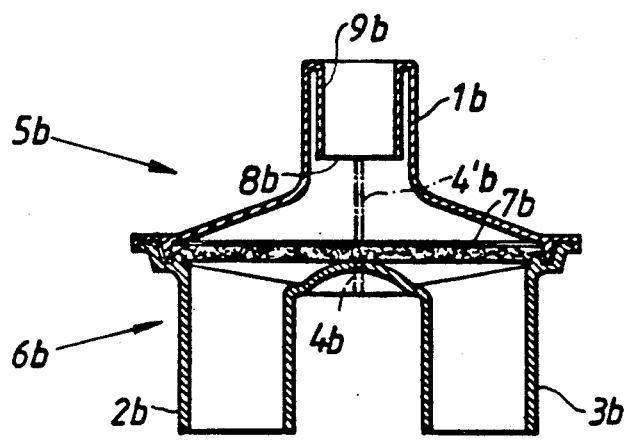
FIG. 13 is a side, elevational, sectional view of another apparatus in accordance with the present invention.
Figure 14:
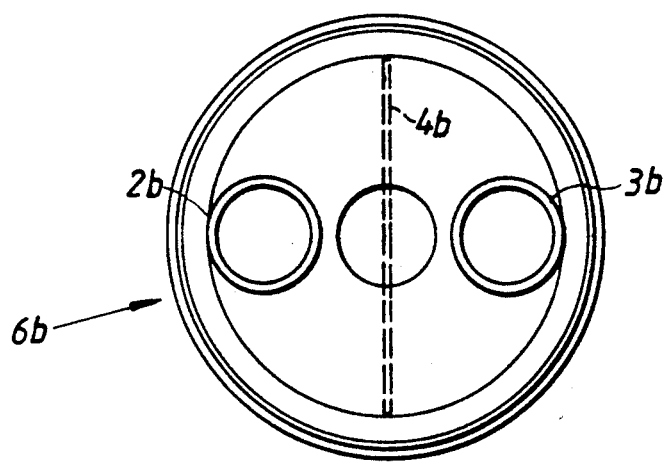
FIG. 14 is a bottom, elevational view of the apparatus shown in FIG. 13.
Figure 15:
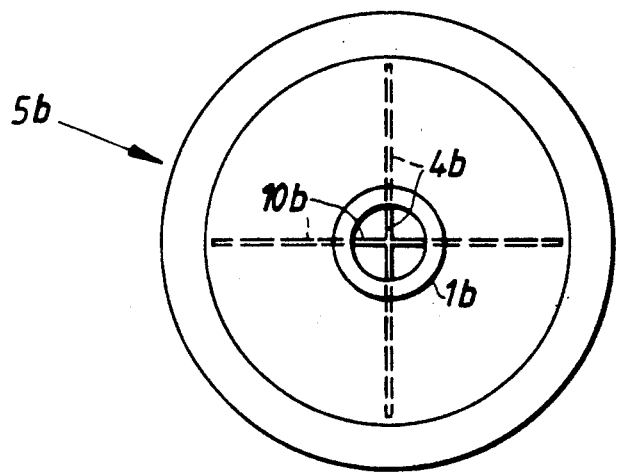
FIG. 15 is a top, elevational view of the apparatus shown in FIG. 13.

Turning next to FIGS. 13 through 15, a preferred embodiment of the connection arrangement according to the present invention is shown. Even though this apparatus does not have the shape of a conventional "Y," in practice it is still referred to as a "Y-piece." This Y-piece comprises an attachment nipple 1b which is directed towards the patient, and two attachment nipples, 2b and 3b, for connection to an inhalation tube and an exhalation tube, respectively. This construction is also characterized by a partition wall 4b which is arranged to separate inhaled air from exhaled air during their passage through the Y-piece from the inlets for both the attachment nipples, 2b and 3b, to and from the patient attachment nipple 1b.

The construction shown in FIGS. 13 through 15 consists of two parts or halves, 5b and 6b, in which the first part 5b comprises the patient attachment nipple 1b, and the second part 6b comprises the two other nipples, 2b and 3b. A filter 7b is clamped between these two parts. The filter has a porosity such that it does not seriously restrict the flow-through of inhaled air, but nevertheless stops bacteria.

The partition wall 4b should extend at least up to the filter 7b. Preferably, however, it continues with an extension portion 4'b into the part 5b, and preferably up to the inner edge 8b of an inwardly directed collar 9b in the patient attachment nipple 1b. This collar 9b facilitates connection of this apparatus to attachment parts having various different size, either interiorly or exteriorly. If the partition wall 4'b extends into the collar 9b, then internal attachment is hindered. However, it is still possible to effect external attachment at the same time that the dead volume of the Y-piece can be said to be zero, or substantially zero. If the part 5b is provided with a partition wall 4'b, then under all circumstances this should extend through the space between the collar 9b and the nipple 1b.

In FIG. 15, it is noted that the part 5b can be provided with a further partition wall 10b. This does not separate the inhaled and exhaled air, but is instead intended to merely support the filter 7b. The part 6b can also be provided with such a supporting partition wall. this is, however, not shown in this embodiment.

A Y-piece substantially corresponding to FIGS. 13-15 with the partition walls 4b and 4'b, was compared to a conventional Y-piece. Thereafter, a corresponding Y-piece without partition walls was compared with similar conventional Y-pieces. The comparison showed that the embodiment with partition walls had substantially the same dead volume as a conventional Y-piece. Corresponding Y-pieces without partition walls, however, had an increased dead volume in relation to the conventional Y-piece.

FIGS. 16 through 18 show another embodiment of the present invention. This embodiment corresponds in principle with that according to FIGS. 13 through 15, and the same reference numerals have thus been used, but with the suffix c in this case. The two joined parts or halves are thus denoted by 5c and 6c, respectively. The part 5c includes the patient attachment nipple 1c, and the part 6c includes the two other nipples, 2c and 3c. The partition wall, which is a significant element of the present invention, is denoted by reference numeral 4c, and the supporting partition wall by reference numeral 10c. A filter 7c is clamped between the two parts, 5c and 6c. This embodiment differs from that according to FIGS. 13 through 15 in that it is provided with a sample withdrawal outlet 11c arranged between the two nipples, 2c and 3c. This sample withdrawal outlet 11c is extended by a sample withdrawal tube 12c, which extends up to the filter 7c. On the other side of the filter, a second sample withdrawal tube 13c continues and extends up to the outer orifice of the patient attachment nipple 1c. Both the sample withdrawal tubes 12c and 13c are formed in one piece with the partition wall 4c. In this manner, and by use of a suitable design, the two parts 5c and 6c are given a suitable shape for injection molding. They can thus be injection molded with the air of relatively simple equipment.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. Apparatus for connecting a patient to breathing device comprising a patient attachment tube member extending in a first direction and having a first end and a second end, first and second attachment tube members extending in a second direction, said first and second attachment tube members adapted for connection to an inhalation tube and an exhalation tube, respectively, and each including a first end and a second end, said second direction being different from said first direction such that said first end of said patient attachment tube member is proximate to said first ends of said first and second attachment tube members and said second end of said patient attachment tube member is distal from said second ends of said first and second attachment tube members, connecting means connecting said first end of said patient attachment tube member to said first ends of said first and second attachment tube members, a bacteria filter disposed within said apparatus and separating said first end of said patient attachment tube member from said first ends of said first and second attachment tube members, whereby gases passing between said patient attachment tube member and said first and second attachment tube members along a predetermined flow path must pass through said bacteria filter, and a patient attachment element attached to said patient attachment tube member, said patient attachment element comprising a wad of flexible material comprising fibers of plastic material having a first melting point, coated with a plastic material having a second melting point, said second melting point being lower than said first melting point so that said fibers may be bonded by heating said fibers to said second melting point.

2. The apparatus of claim 1 wherein said patient attachment tube member comprises a first part of said apparatus, and said first and second attachment tube members comprise a second part of said apparatus, said first and second parts being attached to each other to form said connecting means with said bacteria filter therebetween.

3. The apparatus of claim 1 wherein said patient attachment tube member and said first and second attachment tube members comprise nipples extending substantially parallel to each other.

4. The apparatus of claim 1 wherein said apparatus has a substantially circular configuration so as to maximize the flow-through area of said apparatus in proportion to the volume of said apparatus.

5. The apparatus of claim 1 including sample withdrawal means for obtaining a gas sample from said apparatus during exhalation therethrough.

6. The apparatus of claim 5 wherein said sample withdrawal means is located on the opposite side of said bacteria filter as compared to said patient attachment tube member.

7. The apparatus of claim 6 wherein said sample withdrawal means includes first tube means extending into contact with said bacterial filter.

8. The apparatus of claim 7 wherein said sample withdrawal means includes second tube means located on the same side of said bacteria filter as said patient attachment tube member, and wherein said second tube means extends into contact with said bacteria filter.

9. The apparatus of claim 8 wherein said second tube means extends into said patient attachment tube member.

10. The apparatus of claim 8 wherein said first and second tube means are located on opposite sides of said bacteria filter and in pressure contact therewith.

11. The apparatus of claim 10 wherein said first and second tube means each include widened portions at the ends of said first and second tube means in contact with said bacteria filter.

12. The apparatus of claim 11 wherein said widened portions comprise cone-shaped or cylindrical configurations.

13. The apparatus of claim 5 wherein said patient attachment tube member comprises a first part of said apparatus and said first and second attachment tube members comprise a second part of said apparatus, said first and second part being attached to each other to form said connecting means with said bacteria filter therebetween.

14. The apparatus of claim 13 wherein said sample withdrawal means is provided between said first and second attachment tube members.

15. The apparatus of claim 14 wherein said sample withdrawal means extends in said second direction.

16. The apparatus of claim 15 wherein said first and second parts has a substantially oval configuration.

17. The apparatus of claim 15 wherein said first and second parts has a substantially rectangular configuration including rounded corners.

18. The apparatus of claim 14 wherein said sample withdrawal means comprises a nipple.

19. The apparatus of claim 13 wherein said first and second parts include bowl-shaped inner surfaces in contact with said bacteria filter, and wherein at least said second part includes web means for supporting said sample withdrawal means therein.

20. The apparatus of claim 19 wherein both said first and second parts include web means for supporting said sample withdrawal means.

21. The apparatus of claim 13 wherein said sample withdrawal means extends from said second part, and wherein said connecting means includes a concave portion surrounding said sample withdrawal means so as to stabilize said sample withdrawal means and reduce the inner volume of said apparatus therebelow.

22. The apparatus of claim 1 wherein said patient attachment element comprises a flexible tubular member.

23. The apparatus of claim 1 wherein said wad of flexible material is impregnated with a material selected from the group consisting of anti-bacterial agents and hygroscopic substances.

24. The apparatus of claim 23 wherein said anti-bacterial agents are selected from the group consisting of clorhexidine and hydrogen peroxide and said hygroscopic substance is selected from the group consisting of magnesium chloride, lithium chloride and calcium chloride.

25. The apparatus of claim 1 wherein said fibers of plastic material having a first melting point comprise polypropylene and said plastic material having a second melting point comprises polyethylene.

26. The apparatus of claim 1 wherein said patient attachment element includes at least a portion comprising transparent material, which portion is free of any added material on the interior thereof so as to serve as a secretion trap or inspection zone therefor.

27. The apparatus of claim 1 wherein said patient attachment element is disconnectable from said patient attachment tube member.

28. The apparatus of claim 1 including partition means extending from a point between said first and second attachment tube members towards said patient attachment tube member so as to separate inhaled air and exhaled air during their respective passage through said apparatus in said predetermined flow direction.

29. The apparatus of claim 28 wherein said partition means extends at least up to said bacteria filter.

30. The apparatus of claim 28 wherein said patient attachment tube member comprises a first part of said apparatus, and said first and second attachment tube members comprise a second part of said apparatus, said first and second parts being attached to each other to form said connecting means with said bacteria filter therebetween, said partition means being contained within said second part and extending towards said filter.

31. The apparatus of claim 30 wherein both said first and second parts include partition means, whereby said partition means is located on either side of said bacteria filter so as to clamp and support that bacteria filter therebetween.

32. The apparatus of claim 31 wherein said partition means on both said first and second parts include a first partition means portion and a second partition means portion.

33. The apparatus of claim 30 wherein said first and second parts have substantially circular configuration.

34. The apparatus of claim 33 wherein said bacteria filter has a circular configuration.

35. The apparatus of claim 28 wherein said patient attachment tube member includes a collar member concentrically located therewithin for facilitating connection to various attachment parts, either exteriorly or interiorly of said patient attachment tube member, said partition means extending only between said collar member and said patient attachment tube member.

36. The apparatus of claim 28 including sample withdrawal means.

37. The apparatus of claim 36 wherein said sample withdrawal means is affixed to said second part and includes a sample withdrawal tube extending within said second part towards said bacteria filter.

38. The apparatus of claim 37 wherein said sample withdrawal tube is in direct contact with said bacteria filter, whereby any sample passing through said sample withdrawal tube must pass through said bacteria filter.

39. The apparatus of claim 38 wherein said sample withdrawal tube comprises a first sample withdrawal tube, and including a second sample withdrawal tube contained in said first part, whereby said first and second sample withdrawal tubes are juxtaposed on opposite sides of said bacteria filter.

40. The apparatus of claim 39 wherein said second sample withdrawal tube extends into said patient attachment tube member.

41. The apparatus of claim 36 wherein said sample withdrawal means forms a portion of said partition means.

42. Apparatus for connecting a patient to breathing devices comprising a patient attachment element, a Y-piece for connecting said patient attachment element to an inhalation tube and an exhalation tube, said Y-piece including inherent dead volume a bacteria filter comprising a filtering medium therein, and means for withdrawing a gas sample without increasing the dead volume of said Y-piece, said withdrawing means comprising a sample withdrawal member located downstream of said bacteria filter with respect to said patient attachment element, said sample withdrawal member including a sample withdrawal tube extending towards said bacteria filter for contact with said filtering medium so that bacteria-free samples can be obtained from said sample withdrawal means through said bacteria filter without increasing the dead volume of said Y-piece.

43. The apparatus of claim 42 wherein said sample withdrawal tube comprises a first sample withdrawal tube, and including a second sample withdrawal tube on the opposite side of said bacteria filter with respect to said first sample withdrawal tube, said second sample withdrawal tube extending towards said patient attachment element.

44. The apparatus of claim 43 wherein second sample withdrawal tube extends into said patient attachment element.

45. The apparatus of claim 43 wherein said first and second sample withdrawal tubes are located on opposite sides of said bacteria filter and are in pressure contact with said filtering medium.

46. The apparatus of claim 45 wherein said first and second sample withdrawal tubes each include widened portions on their ends in contact with said filtering medium located within said Y-piece.

47. The apparatus of claim 46 wherein said widened portions of said first and second sample withdrawal tubes comprise cone-shaped or cylindrical portions.

48. The apparatus of claim 42 wherein said patient attachment element comprises a flexible tubular element.

49. The apparatus of claim 48 wherein said patient attachment element includes a heat and moisture exchange medium.

50. The apparatus of claim 49 wherein said heat and moisture exchange medium comprises a wad of flexible material.

51. The apparatus of claim 50 wherein said wad of flexible material comprises fibers.

52. Apparatus for connecting a patient to breathing devices, said apparatus having inherent dead volume, and in comprising a patient attachment tube member extending in a first direction and having a first end and a second end, first and second attachment tube members extending in a second direction, said first and second attachment tube members adapted for connection to an inhalation tube and an exhalation tube, respectively, and each including a first end and a second end, said second direction being different from said first direction such that said first end of said patient attachment tube member is proximate to said first ends of said first and second attachment tube members and said second end of said patient attachment tube member is distal from said second ends of said first and second attachment tube members, connecting means connecting said first end of said patient attachment tube member to said first ends of said first and second attachment tube members, a bacteria filter comprising a filter medium therein disposed within said apparatus and separating said first end of said patient attachment tube member from said first ends of said first and second attachment tube members, whereby gases passing between said patient attachment tube member and said first and second attachment tube members along a predetermined flow path must pass through said filter medium of said bacteria filter, means for withdrawing a gas sample and for reducing the dead volume of said apparatus, said sample withdrawal means located on the opposite side of said bacteria filter as compared to said patient attachment tube member and including first tube means extending into contact with said filter medium of said bacteria filter for obtaining a gas sample from said apparatus during exhalation therethrough, and a patient attachment element attached to said patient attachment tube member comprising a flexible tubular member and including a heat and moisture exchange medium therein.

53. The apparatus of claim 52 wherein said patient attachment tube member comprises a first part of said apparatus, and said first and second attachment tube members comprise a second part of said apparatus, said first and second parts being attached to each other to form said connecting means with said bacteria filter therebetween.

54. The apparatus of claim 52 wherein said patient attachment tube member and said first and second attachment tube members comprise nipples extending substantially parallel to each other.

55. The apparatus of claim 52 wherein said heat and moisture exchange medium comprises a wad of flexible material.

56. The apparatus of claim 55 wherein said wad of flexible material comprises fibers.

57. The apparatus of claim 52 wherein said sample withdrawal means includes second tube means located on the same side of said bacteria filter as said patient attachment tube member, and wherein said second tube means extends into contact with said bacteria filter.

58. The apparatus of claim 57 wherein said second tube means extends into said patient attachment tube member.

59. The apparatus of claim 52 including partition means extending from a point between said first and second attachment tube members towards said patient attachment tube member so as to separate inhaled air and exhaled air during their respective passage through said apparatus in said predetermined flow direction.

60. The apparatus of claim 59 wherein said partition means extends at least up to said bacteria filter.

61. Apparatus for connecting a patient to breathing devices, said apparatus having an inherent dead volume and comprising a patient attachment tube member extending in a first direction and having a first end and a second end, first and second attachment tube members extending in a second direction, said first and second attachment tube members adapted for connection to an inhalation tube and an exhalation tube, respectively, and each including a first end and a second end, said second direction being different from said first direction such that said first end of said patient attachment tube member is proximate to said first ends of said first and second attachment tube members and said second end of said patient attachment tube member is distal from said second ends of said first and second attachment tube members, connecting means connecting said first end of said patient attachment tube member to said first ends of said first and second attachment tube members, a bacteria filter including a filtering medium therein disposed within said connecting means, whereby gases passing between said patient attachment tube member and said first and second attachment tube members along a predetermined flow path must pass through said bacteria filter, and means for withdrawing a gas sample and for reducing the dead volume of said apparatus, said sample withdrawal means located on the opposite side of said bacteria filter as compared to said patient attachment member for obtaining a gas sample from said apparatus during exhalation therethrough, said sample withdrawal means including first tube means extending into contact with said filtering medium of said bacteria filter.

62. The apparatus of claim 61 including a patient attachment element attached to said patent attachment tube member for use by said patient, and wherein said apparatus has a flow-through area which is greater than the flow-through area of said patient attachment element.

63. The apparatus of claim 61 wherein said patient attachment tube member comprises a first part of said apparatus, and said first and second attachment tube members comprise a second part of said apparatus, said first and second parts being attached to each other to form said connecting means with said bacteria filter therebetween.

64. The apparatus of claim 63 wherein said sample withdrawal means is provided between said first and second attachment tube members.

65. The apparatus of claim 61 including a patient attachment element comprising a flexible tubular member attached to said patient attachment tube member.

66. The apparatus of claim 65 wherein said patient attachment element includes a heat and moisture exchange medium therein.

67. The apparatus of claim 66 wherein said heat and moisture exchange medium comprises a wad of flexible material.

68. The apparatus of claim 61 wherein said sample withdrawal means includes second tube means located on the same side of said bacteria filter as said patient attachment tube member, and wherein said second tube means extends into contact with said bacteria filter.

69. The apparatus of claim 68 wherein said second tube means extends into said patient attachment tube member.

70. Apparatus for connecting a patient to breathing devices comprising a patient attachment tube member extending in a first direction and having a first end and a second end, first and second attachment tube members extending in a second direction, said first and second attachment tube members adapted for connection to an inhalation tube and an exhalation tube, respectively, and each including a first end and a second end, said second direction being different from said first direction such that said first end of said patient attachment tube member is proximate to said first ends of said first and second attachment tube members and said second end of said patient attachment tube member is distal from said second ends of said first and second attachment tube members, connecting means connecting said first end of said patient attachment tube member to said first ends of said first and second attachment tube members, a bacteria filter disposed within said apparatus and separating said first end of said patient attachment tube member from said first ends of said first and second attachment tube members, whereby gases passing between said patient attachment tube member and said first and second attachment tube members along a predetermined flow path must pass through said bacteria filter, and partition means extending from said bacteria filter to a point between said first and second attachment tube members on a first side of said filter, and towards said patient attachment tube member on a second side of said filter, so as to separate inhaled air and exhaled air during their respective passage through said apparatus in said predetermined flow direction.

71. The apparatus of claim 69 wherein said patient attachment tube member comprises a first part of said apparatus, and said first and second attachment tube members comprise a second part of said apparatus, said first and second parts being attached to each other to form said connecting means with said bacteria filter therebetween.

72. The apparatus of claim 71 including sample withdrawal means.

73. The apparatus of claim 72 wherein said sample withdrawal means is affixed to said second part and includes a sample withdrawal tube extending within said second part towards said bacteria filter.

74. The apparatus of claim 73 wherein said sample withdrawal tube is in direct contact with said bacteria filter, whereby any sample passing through said sample withdrawal tube must pass through said bacteria filter..

75. The apparatus of claim 74 wherein said sample withdrawal tube comprises a first sample withdrawal tube, and including a second sample withdrawal tube contained in said first part, whereby said first and second sample withdrawal tubes are juxtaposed on opposite sides of said bacteria filter.

76. The apparatus of claim 75 wherein said second sample withdrawal tube extends into said patient attachment tube member.

77. The apparatus of claim 70 including a patient attachment element attached to said patient attachment tube member.

78. The apparatus of claim 77 wherein said patient attachment element comprises a flexible tubular member.

79. The apparatus of claim 77 wherein said patient attachment element includes a heat and moisture exchange medium therein.

80. The apparatus of claim 79 wherein said heat and moisture exchange medium comprises a wad of flexible material.

81. The apparatus of claim 80 wherein said wad of flexible material comprises fibers.

* * * * *

UNITED STATES PATENT AND TRADEMARK OFFICE
CERTIFICATE OF CORRECTION

PATENT NO.  : 5,213,096
DATED       : May 25, 1993
INVENTOR(S) : Ake Kihlberg, Ragnar Tryggvason, Per Wikefeldt It is certified that error appears in the above-identified patent and that said Letters Patent is hereby corrected as shown below:

```
Column 8,   line 21, "25'" should read --25"--.
            line 23, "14'" should read --14"--.
            line 26, "16'" should read --16"--.
Column 13,  line 40, delete "in".
Column 15,  line 4, delete "patent" and insert therefor
            --patient--.
Column 16,  line line 13, delete "69" and insert therefor --70--.
```

Signed and Sealed this

First Day of February, 1994

Attest:

BRUCE LEHMAN

Attesting Officer

Commissioner of Patents and Trademarks